US005554385A

United States Patent [19]

Stroud

[11] Patent Number: 5,554,385

[45] Date of Patent: Sep. 10, 1996

[54] HIGH AMYLOSE STARCH SUBSTITUTED GELATIN CAPSULES

[75] Inventor: Norman Stroud, Corsham, England

[73] Assignee: R. P. Scherer Corporation, Troy, Mich.

[21] Appl. No.: 343,185

[22] Filed: Nov. 22, 1994

Related U.S. Application Data

[63] Continuation of Ser. No. 619,133, Nov. 28, 1990, abandoned.

[51] Int. Cl.[6] .................................................... A61K 9/48

[52] U.S. Cl. ......................... 424/456; 424/451; 424/452; 514/962

[58] Field of Search .................................. 424/456, 451, 424/452

[56] References Cited

U.S. PATENT DOCUMENTS 4,673,438 6/1987 Wittwer et al. ......................... 166/126

*Primary Examiner*—Edward J. Webman
*Attorney, Agent, or Firm*—Banner & Allegretti, Ltd.

[57] ABSTRACT

A gelatin capsule sheath in which a portion of the gelatin is replaced with a high amylose content starch to provide a dry capsule sheath having 3–60% by weight high amylose starch wherein the amylose content of the starch is at least 50% and preferably 90% high amylose starch. The capsules of this invention have textured frosted or satin finish which do not stick together, form strong seals, are resistant to changes in shape, and are more economical to manufacture.

4 Claims, No Drawings

HIGH AMYLOSE STARCH SUBSTITUTED GELATIN CAPSULES

This is a continuation of application Ser. No. 07/619,133, filed Nov. 28, 1990, now abandoned.

FIELD OF INVENTION

The present invention relates to gelatin capsules wherein the dry capsule sheath comprises typically 3–60% of a starch having a high amylose content. The capsule sheath also contains other additives such as plasticizers to prevent brittle fracture. The capsule filling may comprise therapeutic agents, dietetic agents and the like.

BACKGROUND OF THE INVENTION

Soft gelatin capsules comprising principally gelatin, glycerol and water are used for the administration of solids, masses and liquids. They are desirable dosage forms for the administration of many therapeutic substances such as drugs having a bitter taste or are in liquid form. In addition, the gelatin shell wall being readily soluble in the stomach, the contents are more readily absorbed due to the absence of excipients usually present in other oral dosage forms such as tablets and pills. Soft gelatin capsules are particularly suitable for dispensing liquids such as fixed and volatile oils.

The preparation of soft gelatin capsules is described, for example, in Lachman, *Theory and Practice of Industrial Pharmacy*, Lea & Febiger, Philadelphia, Second Edition, 1986.

U.S. Pat. No. 4,804,542 discloses a soft gelatin capsule consisting of a capsule sheath and a capsule filling wherein the capsule sheath consisting of gelatin and a small amount additive in the sheath such as starch, starch derivative, cellulose, cellulose derivative, milk product and so on.

In the usual practice, the empty soft gelatin capsule is filled with the desired material. Thereafter, the empty gelatin capsule is sealed.

SUMMARY OF THE INVENTION

A new capsule sheath material for making the soft gelatin capsule has been discovered. In this sheath a substantial part of gelatin is replaced with a high amylose starch. The dry capsule contains 3–60% high amylose starch and the high amylose starch contains at least 50% preferably 90% amylose. The soft gelatin capsule comprising this sheath material is manufactured in accordance with known procedures such as that described in U.S. Pat. Nos. 4,804,542 or 4,744,988.

The soft gelatin capsules prepared in accordance with this invention are characterized as having a textured frosted or satin finish depending on the starch selected. The surface of the capsule in contrast to prior art soft gelatin capsules is rougher thereby preventing the gelatin capsules from sticking especially during storage under humid conditions.

DETAILED DESCRIPTION OF THE INVENTION

The present invention relates to soft gelatin capsules wherein a substantial part of gelatin is replaced by starch having a high amylose content.

Starch is the most common carbohydrate reserve found in varying amounts in almost all plant members. Starch of commerce, from whatever source it may have been extracted, consists of two or three chemically individual substances all closely related to the sugars distributed throughout the body of the starch granule in different physical states. The important constituents are amylose, amylopectin and amylo-hemicellulose. The first two constituents are present in all starches while the third is found in certain starches such as those derived from graminaceous seeds. Amylose is essentially a linear or partially branched polymer of alpha (1–4) D-glucose, amylopectin is a densely branched, high molecular weight polymer of alpha (1–4) and (1–6) linked glucose units. The molecular weights are I–5×$10^5$ Daltons and I–50×$10^7$ Daltons respectively for amylose and amylopectin. Amylose constitutes the film forming (gel-forming) component of starches.

Starch of high amylose content is indicated as the starch to be incorporated in the capsule sheath of the present invention. The term "high amylose starch" refers to those starches having an amylose content of at least 50% and those having 90% or more is most preferred. "Gelatin" as used herein includes those obtained from animal sources as well as modified gelatin such as succinated gelatin. When high amylose starch is incorporated in the capsule sheath, the resulting capsule exhibits a textured frosted or satin finish. This surface is quite advantageous if the capsule is to be coated with an enteric coating and possesses very strong seals. Moreover, such a capsule containing a high starch content allows the successful encapsulation of products having an appreciable level of water. Furthermore, such capsules have been shown to be much more resistant to changes in capsule shape than normal gelatin capsules during extended storage. From a cost point of view, starch is much cheaper than gelatin, and a considerable benefit in terms of a cost savings can readily be achieved.

Among the starches having high amylose content are, for example, potato starch, maranta starch or those available commercially under the tradename Amylose PF from Tunnel-Avebe or Hylon VII starches from National Starch.

In accordance with the present invention, there is provided a soft gelatin capsule wherein as high as 85% of the gelatin in the sheath is replaced with a high amylose starch.

Table I illustrates typical substitutions of starch for gelatin, in accordance with the present invention, first in the initial formulation composition (A), dry capsule shell composition (B), and capsule shell containing about 6% water (C).

TABLE 1

COMPOSITION BY WEIGHT OF CAPSULE SHELL FORMULATIONS

A. Initial Formulation Composition

| | % Substitution | | | | | | | | | | |
|---|---|---|---|---|---|---|---|---|---|---|---|
| | 0 | 5 | 10 | 15 | 25 | 35 | 45 | 55 | 65 | 75 | 85 |
| Gelatin | 44 | 41.8 | 39.6 | 37.4 | 33.0 | 28.6 | 24.2 | 19.8 | 15.4 | 11.0 | 6.6 |
| Starch | 0 | 2.2 | 4.4 | 6.6 | 11.0 | 15.4 | 19.8 | 24.2 | 28.6 | 33.0 | 37.4 |
| Glycerol | 20 | → | → | → | → | → | → | → | → | → | → |

TABLE 1-continued

COMPOSITION BY WEIGHT OF CAPSULE SHELL FORMULATIONS

| | | | | | | | | | | | |
|---|---|---|---|---|---|---|---|---|---|---|---|
| Water | 36 | → | → | → | → | → | → | → | → | → | → |
| B. Dry Capsule Composition (Anhydrous Shell) | | | | | | | | | | | |
| | % Substitution | | | | | | | | | | |
| | 0 | 5 | 10 | 15 | 25 | 35 | 45 | 55 | 65 | 75 | 85 |
| Gelatin | 68.75 | 65.31 | 61.87 | 58.43 | 51.55 | 44.67 | 37.79 | 30.91 | 24.03 | 17.15 | 10.27 |
| Starch | 0 | 3.44 | 6.88 | 10.32 | 17.20 | 24.08 | 30.96 | 37.84 | 44.72 | 51.60 | 58.48 |
| Glycerol | 31.25 | → | → | → | → | → | → | → | → | → | → |
| C. Dry Capsule Composition - Approximately 6% Water | | | | | | | | | | | |
| | % Substitution | | | | | | | | | | |
| | 0 | 5 | 10 | 15 | 25 | 35 | 45 | 55 | 65 | 75 | 86 |
| Gelatin | 64.61 | 61.38 | 58.15 | 54.92 | 48.46 | 42.0 | 35.54 | 29.08 | 22.62 | 16.16 | 9.70 |
| Starch | 0 | 3.23 | 6.46 | 9.69 | 16.15 | 22.61 | 29.07 | 35.53 | 41.99 | 48.45 | 54.91 |
| Glycerol | 29.37 | → | → | → | → | → | → | → | → | → | → |
| Water | 6.02 | → | → | → | → | → | → | → | → | → | → |

The selected high amylose starch, or a suspension of the starch in water or glycerin, is added to a solution of gelatin, glycerin and water. The resultant mixture is heated and blended until a homogenous mixture is obtained. Soft gelatin capsules are prepared from such a mixture, e.g. by the rotary-die encapsulation process.

The soft gelatin capsules thus produced generally has a rough surface depending on the starch selection which will allow them to be packed together without the tendency to stick together as commonly occurs with 100% gelatin capsules.

In order to further illustrate the practice of this invention, the following examples are included.

EXAMPLE 1

A gelatin solution is prepared by mixing together 31.2 kg of gelatin, 16 kg of glycerol and 36 kg potable water. To this there is added 16.8 kg of Amylose PF having an amylose content of at least 90%. Oblong shaped gelatin capsules are prepared from this mixture in which 35% of the gelatin in the capsule sheath is replaced by starch and the capsule wall has a thickness of about 0.030 inches.

The capsules are filled with liquid paraffin and sealed. These capsules rupture and the walls dissolve within 30 minutes in water.

EXAMPLE 2

A similar formulation using Hylon VII starch in lieu of Amylose PF wherein the amylose content is 70%. The resulting capsules possess both strong seals and good shapes. The finished (dry) capsules possess a smooth, opaque satin finish. The capsules are filled with liquid paraffin and stored at 40 degrees C. for 4 months. New capsules rupture within 1.6 minutes and the walls dissolve within 6.2 minutes.

EXAMPLE 3

Similar capsules are prepared as in Example 1 with the exception Hylon V starch having a 50% amylose content is employed.

EXAMPLE 4

STARCH-EXTENDED GELATIN FORMULATIONS

Typical Formulation 85% Substitution of Gelatin are as follows:

| | | |
|---|---|---|
| Initial Composition | | |
| Gelatin | 6.6 | |
| Starch | 37.4 | |
| Glycerol | 20.0 | |
| Water | 36.0 | |
| | 100.00 | |
| Dry Capsule Composition - Anhydrous | | |
| | | % |
| Gelatin | 6.6 | 10.3 |
| Starch | 37.4 | 58.4 |
| Glycerol | 20.0 | 31.3 |
| | 64.0 | |
| Dry Capsule Composition - 6% Water in Shell | | |
| Gelatin | 6.6 | 9.69 |
| Starch | 37.4 | 14.92 |
| Glycerol | 20.0 | 29.37 |
| Water | 4.1 | 6.02 |
| | 68.1 | 100.00 |

I claim:

1. A soft gelatin capsule made by the rotary-die encapsulation process in which the dry capsule sheath comprises 3–60% of high amylose starch wherein the high amylose starch has from 50% to about 90% amylose content.

2. A soft gelatin capsule according to claim 1 comprising by weight 3 to 60% high amylose starch, 65 to 10% gelatin, and about 31% glycerol.

3. The soft gelatin capsule according to claim 1 made by the rotary die encapsulation process comprising by weight 3 to 55% high amylose starch, 60 to 10% gelatin, about 30% glycerol and about 6% water wherein the high amylose starch contains 50% to about 90% amylose.

4. A soft gelatin capsule according to claim 1 wherein the amylose content of the high amylose starch is at least 90%.

* * * * *